(12) United States Patent
Yun et al.

(10) Patent No.: US 10,899,849 B2
(45) Date of Patent: Jan. 26, 2021

(54) METHOD FOR THE PRODUCTION OF PULLULAN CAPSULES

(71) Applicant: LEFAN CAPSULE INTERNATIONAL INC, Ontario, CA (US)

(72) Inventors: Xianyu Yun, Zhenjiang (CN); Sheng Wang, Zhenjiang (CN); Zhongming Fang, Zhenjiang (CN); Fei Wang, Zhenjiang (CN); Peiyong Liu, Zhenjiang (CN); Xiaosan Cao, Zhenjiang (CN); Zhidong Lu, Zhenjiang (CN)

(73) Assignee: LEFAN CAPSULE INTERNATIONAL INC, Ontario, CA (US)

( * ) Notice: Subject to any disclaimer, the term of this patent is extended or adjusted under 35 U.S.C. 154(b) by 0 days.

(21) Appl. No.: 16/398,712

(22) Filed: Apr. 30, 2019

(65) Prior Publication Data

US 2020/0347154 A1    Nov. 5, 2020

(51) Int. Cl.
| | |
|---|---|
| *C08B 37/00* | (2006.01) |
| *C12P 19/10* | (2006.01) |
| *B01J 41/12* | (2017.01) |
| *B01J 39/18* | (2017.01) |

(52) U.S. Cl.
CPC .......... *C08B 37/0018* (2013.01); *C12P 19/10* (2013.01); *B01J 39/18* (2013.01); *B01J 41/12* (2013.01)

(58) Field of Classification Search
None
See application file for complete search history.

(56) References Cited

U.S. PATENT DOCUMENTS

| | | | |
|---|---|---|---|
| 8,821,934 B2 | 9/2014 | Sugimoto et al. | |
| 8,900,629 B2 * | 12/2014 | Rajewski | A61K 9/0056 424/452 |
| 2005/0249676 A1 | 11/2005 | Scott et al. | |
| 2007/0059355 A1 | 3/2007 | Madit | |
| 2011/0171281 A1 | 7/2011 | Cao | |
| 2014/0112982 A1 | 4/2014 | Cao et al. | |
| 2018/0154327 A1 | 6/2018 | Liu et al. | |

FOREIGN PATENT DOCUMENTS

| | | |
|---|---|---|
| CN | 1106448 C | 4/2003 |
| CN | 102586088 B | 4/2013 |
| WO | 2018189584 A9 | 1/2017 |

OTHER PUBLICATIONS

Yu et al.,"Media optimization for elevated molecular weight and mass production of pigment-free pullulan", Carbohydrate Polymers 89: 928-934. (Year: 2012).*
Cheng et al.,"Pullulan: biosynthesis, production, and applications", Appl. Microbiol. Biotechnol. 92: 29-44. (Year: 2011).*
NPcaps® product sheet (downloaded on Apr. 14, 2008 from website www.capsugel.com/products/npcaps.php (Year: 2008).*
NPcaps product sheet attachement (Year: 2012).*
International Search Report dated Aug. 10, 2020 from PCT Application No. PCT/US2020/035909.
International Search Report dated Jun. 25, 2020 from PCT Application No. PCT/US2020/028000.

* cited by examiner

*Primary Examiner* — Anandu U Desai
(74) *Attorney, Agent, or Firm* — Innovation Capital Law Group, LLP; Vic Lin

(57) ABSTRACT

A method for the production of empty pullulan capsules eliminate the need to dry pullulan solid product, thereby reducing the equipment cost and energy consumption. The pullulan raw material production can be linked directly with the capsule production to provide a unique approach for empty capsule formation. The purified pullulan fermentation fluid can be directly used in capsule preparation, thus removing the need for a melting process. On the one hand, the method may decrease material consumption, save the cost of equipment and labor, reduce production time and increase productivity. On the other hand, the method may reduce the fluctuating of raw material quality in the re-melting process and guarantee a more stable capsule production and quality.

16 Claims, 1 Drawing Sheet

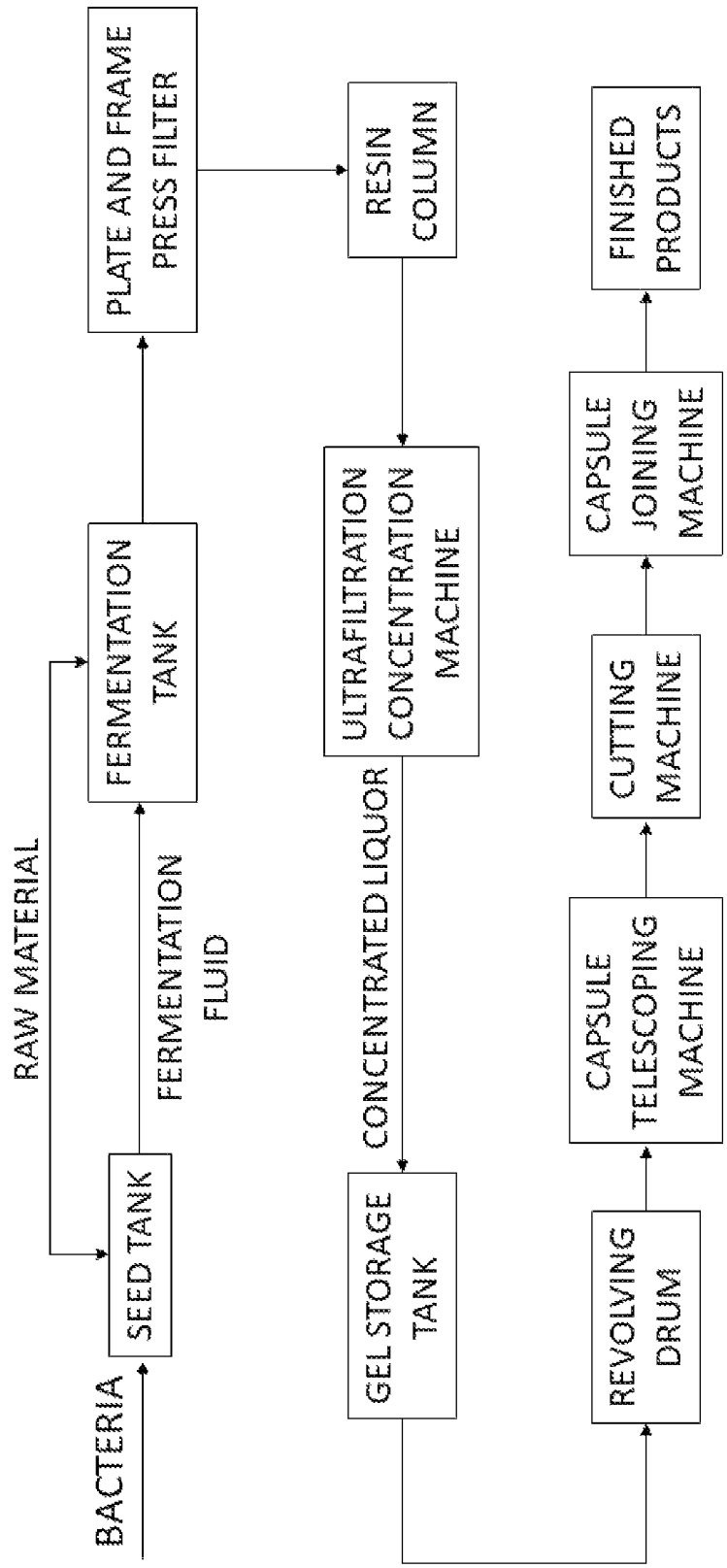

METHOD FOR THE PRODUCTION OF PULLULAN CAPSULES

BACKGROUND OF THE INVENTION

1. Field of the Invention

Embodiments of the invention relates generally to capsule production methods. More particularly, the invention relates to a method for the production of empty capsules formed from pullulan, from raw material to final product.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Pullulan is a polysaccharide polymer of a maltotriose trimer made up of α-(1→6)-linked (1→4)-α-d-triglucosides, also known as α-1,4-α-1,6-glucan. Three glucose units in maltotriose are connected by an α-1,4 glycosidic bond, whereas consecutive maltotriose units are connected to each other by an α-1,6 glycosidic bond. Pullulan is produced from starch by the fungus Aureobasidium pullulans.

Pullulan is a natural raw material of vegetable capsules with excellent film-forming property, water solubility, biological compatibility, and degradability. However, the production level of this product is low worldwide. In the production of pullulan, the drying process has high requirements on equipment and the energy consumption is large. If the fermentation can't match with the drying production capacity, it will seriously restrict the pullulan production capacity, thus finally restrains the application of pullulan empty capsules.

Conventionally, pullulan is produced by mesophilic fermentation of starch syrup by the selected non-toxigenic strain of Aureobasidium pullulans. The strain is selected by traditional techniques, i.e. the strain is not the product of genetic modification using recombinant technologies. The production strain has a high yield of pullulan, low production of melanin and does not produce aureobasidin A.

After completion of the fermentation, the fungal cells are removed by microfiltration. The cell-free filtrate is heat-sterilized and treated with activated carbon to remove pigments and other impurities by adsorption. The decolorized filtrate is cooled and deionized using cation and anion exchange resins. The deionized solution is concentrated to a solids content of about 12%, treated a second time with activated carbon, and filtered using diatomaceous earth as a filter aid. The filtrate is concentrated by evaporation to a solids content of about 30% and dried in a drum dryer. The dried pullulan is pulverized to a specified particle size and packed in sterilized polyethylene bags. For the formation of capsules, the dried pullulan is melted and formed into the desired capsules.

Currently, the raw material of produced pullulan empty capsules is pullulan dried product, which is the purified fermentation fluid made in the drying process. A study found that microwave drying would make the pullulan film distorted, while both the spray drying and microwave drying would both result in the browning of the raw pullulan material. Therefore, the drying process during the preparation of pullulan raw material reduces its quality and affect the pullulan capsules. In some embodiments, pullulan capsules can be formed from pullulan having the formula $(C_6H_{10}O_5)n$, where n is from 300 to 3000. Such pullulan molecular weight, as well as other suitable molecular weights for pullulan to form capsules have been demonstrated in the art.

In view of the foregoing, there is a need for alternative processes for the production of pullulan empty capsules that addresses the problems outlines above in the conventional methods of pullulan drying.

SUMMARY OF THE INVENTION

In some embodiments of the present invention, one aspect is to reduce the impact of low raw material quality on capsule preparation of pullulan empty capsules by eliminating the separate drying process, which determines the quality of pullulan formed by conventional methods.

In some embodiments of the present invention, another purpose is to reduce the equipment cost and energy consumption in the drying process by linking pullulan raw material production with capsule production. At the same time, by process improvements, the purified pullulan fermentation fluid can be directly used in capsule preparation, thus removing the need for a separate melting process. On the one hand, these improvements may decrease material consumption, save the cost of equipment and labor, reduce production time and increase productivity. On the other hand, these improvements may reduce the fluctuating of raw material quality in the re-melting process and guarantee a more stable capsule production and quality.

Embodiments of the present invention provide a method for the production of a capsule comprising fermenting cells to produce a pullulan fermentation liquor; filtering the fermentation liquor; concentrating the fermentation liquor; transferring the concentrated fermentation liquor into a gel storage tank having a temperature control function; pumping the concentrated fermentation liquor from the gel storage tank into a transfer tank to form a capsule gel liquid; and forming the pullulan capsule from dipping a mold into the capsule gel liquid.

Embodiments of the present invention further provide a method for the production of pullulan capsules comprising fermenting Aureobasidium pullulans to produce a pullulan fermentation liquor; filtering the fermentation liquor through at least one of a plate and frame press filter and an ion exchange column; concentrating the fermentation liquor; transferring the concentrated fermentation liquor into a gel storage tank maintaining a temperature from about 40° C. to about 70° C.; pumping the concentrated fermentation liquor from the gel storage tank into a transfer tank to form a capsule gel liquid; and forming the pullulan capsule from dipping a mold into the capsule gel liquid.

Embodiments of the present invention also provide a pullulan capsule produced by a process comprising fermenting Aureobasidium pullulans to produce a pullulan fermentation liquor; filtering the fermentation liquor; concentrating the fermentation liquor; transferring the concentrated fermentation liquor into a gel storage tank having a temperature control function; pumping the concentrated fermentation liquor from the gel storage tank into a transfer tank to form a capsule gel liquid; and forming the pullulan capsule from dipping a mold into the capsule gel liquid.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the FIGURES of the accompanying drawings, in which like references may indicate similar elements.

The FIG. illustrates a flow chart schematically showing a method for the production of pullulan empty capsules according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the FIGURES or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide methods for the production of empty pullulan capsules that eliminates the need to dry pullulan solid product, thereby reducing the equipment cost and energy consumption. The pullulan raw material production can be linked directly with the capsule production to provide a unique approach for empty capsule formation. The purified pullulan fermentation fluid can be directly used in capsule preparation, thus removing the need for a melting process. On the one hand, the method may decrease material consumption, save the cost of equipment and labor, reduce production time and increase productivity. On the other hand, the method may reduce the fluctuating of raw material quality in the re-melting process and guarantee a more stable capsule production and quality.

Referring now to the FIG., *Aureobasidium pullulans* are fermented and produced at room temperature and atmospheric pressure. The fermentation of *Aureobasidium pullulans* may be performed by known techniques. Its raw materials are sucrose or glucose, some of which are used for the growing consumption of microbial cells, and the rest turns into polysaccharose.

Raw material and water may be placed proportionally into the seed tank and provided with a sterilization treatment. The temperature can be controlled at about 26~30° C. Bacteria can be added to cultivate for 20-22 h, so as to provide sufficient quantity of liquid for the fermentation tank to produce bacteria.

Raw material and nutritive material may be placed proportionally into the fermentation tank. Purified water may then be added. After sterilization, the fermentation liquor may then be added. The temperature is typically controlled at about 26~30° C. The resulting mixture is stirred and cultivated for about 65~75 h. After that, pullulan fermentation liquor will be obtained.

The plate and frame press filter may then be used to filter and substantially remove the bacteria in the fermentation liquor.

The resulting fermentation liquor may be poured into resin column for ion exchange, so as to substantially remove the small amount of small protein and salt content therefrom.

The inlet valve of the filter system can maintain a working pressure of about 0.5 MPA. During the process, purified water can be used to backwash the filter system and the liquor may be concentrated. According to the setting, the mass fraction of the concentrated liquor can be controlled to about 13-25 (w/w) percent.

The concentrated liquor may be transferred into a gel storage tank, which has a temperature control function, so that the liquor will be immersed in the tank at about 40~70° C.

Gelling agents can be placed into a transfer tank. Then, varieties of pigment can be added according to the desired color formulas. The concentrated liquor can then be pumped into the transfer tank and mixed for about 2~4 h and then let stand for about 4~8 h to form capsule gel liquid. The gel liquid can be standing in water at about 40~70° C. for production usage.

After mold dipping into the gel liquid, the machine speed can be about 16~36 mm/second, and the oven temperature is about 25~35° C. Then, it can rotate evenly under the set mechanical drive. The mold can be placed into the kiln to dry. After about 1~3 h drying, a single section of capsules can be removed from the mold with demold equipment.

A cutting machine may be used to cut the capsule single section into a specified length of various sizes.

A capsule jointing machine may be used to joint sections of the same batch together to get capsule finished products.

Many of the above described steps may be performed using equipment that is known in the art. For example, ion exchange resins and filtration devices for processing pullulan are known in the art. Embodiments of the present invention provide a novel method for the production of pullulan capsules that does not require a drying or melting step, as is performed in conventional methods.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A method for the production of a capsule, comprising:
   fermenting *Aureobasidium pullulans* cells to produce a pullulan fermentation liquor;
   filtering the fermentation liquor;
   concentrating the fermentation liquor;
   transferring the concentrated fermentation liquor into a gel storage tank having a temperature control function;
   pumping the concentrated fermentation liquor from the gel storage tank into a transfer tank to form a capsule gel liquid, the capsule gel liquid having pullulan with a molecular weight suitable for the production of the capsule; and
   forming the pullulan capsule from dipping a mold into the capsule gel liquid, wherein the method lacks drying the pullulan to form a solid pullulan product.

2. The method of claim 1, wherein the concentrating the fermentation liquor is performed to provide a mass fraction of about 13 percent to about 25 percent.

3. The method of claim 1, wherein the fermentation is performed at atmospheric pressure and room temperature.

4. The method of claim 1, wherein the step of filtering the fermentation liquor includes a plate and frame press filter to remove bacteria.

5. The method of claim 1, wherein the step of filtering the fermentation liquor includes passing the fermentation liquor through a resin column for ion exchange.

6. The method of claim 1, where the gel storage tank maintains a temperature from about 40° C. to about 70° C.

7. The method of claim 1, further comprising adding a gelling agent to the transfer tank to improve the molding ability of capsule gel liquid.

8. The method of claim 1, wherein the step of forming the capsule includes dipping a mold into the capsule gel liquid, drying the resulting dipped product, striping the dipped product, cutting the dipped product to the desired size, and joining the dipped product together.

9. A method for the production of pullulan capsules, comprising:
   fermenting *Aureobasidium pullulans* to produce a pullulan fermentation liquor;
   filtering the fermentation liquor through at least one of a plate and frame press filter and an ion exchange column;
   concentrating the fermentation liquor;
   transferring the concentrated fermentation liquor into a gel storage tank maintaining a temperature from about 40° C. to about 70° C.;
   pumping the concentrated fermentation liquor from the gel storage tank into a transfer tank to form a capsule gel liquid, the capsule gel liquid having pullulan with a molecular weight suitable for the production of the capsule; and forming the pullulan capsule from dipping a mold into the capsule gel liquid, wherein the method lacks drying the pullulan to form a solid pullulan product.

10. The method of claim 9, wherein the concentrating the fermentation liquor is performed to provide a mass fraction of about 13 percent to about 25 percent.

11. The method of claim 9, wherein the fermentation is performed at atmospheric pressure and room temperature.

12. The method of claim 9, further comprising adding a gelling agent to the transfer tank to improve the molding ability of capsule gel liquid.

13. A pullulan capsule produced by a process comprising:
fermenting *Aureobasidium pullulans* to produce a pullulan fermentation liquor;
filtering the fermentation liquor;
concentrating the fermentation liquor;
transferring the concentrated fermentation liquor into a gel storage tank having a temperature control function;
pumping the concentrated fermentation liquor from the gel storage tank into a transfer tank to form a capsule gel liquid, the capsule gel liquid having pullulan with a molecular weight suitable for the production of the capsule; and forming the pullulan capsule from dipping a mold into the capsule gel liquid, wherein the process lacks drying the pullulan to form a solid pullulan product.

14. The pullulan capsule of claim 13, wherein the concentrating the fermentation liquor is performed to provide a mass fraction of about 13 percent to about 25 percent.

15. The pullulan capsule of claim 13, wherein the step of filtering the fermentation liquor includes a plate and frame press filter to remove bacteria and passing the fermentation liquor through a resin column for ion exchange.

16. The pullulan capsule of claim 13, where the gel storage tank maintains a temperature from about 40° to about 70° C.

* * * * *